128/660

United States Patent [19]
Myers

[11] Patent Number: 4,508,121
[45] Date of Patent: Apr. 2, 1985

[54] APPARATUS FOR MEASUREMENT OF CORNEAL THICKNESS

[75] Inventor: George H. Myers, Maplewood, N.J.

[73] Assignee: Medsys, Inc., Rutherford, N.J.

[21] Appl. No.: 521,132

[22] Filed: Aug. 8, 1983

[51] Int. Cl.³ .................... G01N 29/00; A61B 5/04
[52] U.S. Cl. ........................................ 128/639; 128/660
[58] Field of Search .............. 128/639, 649, 647, 660, 128/774, 745; 73/628, 629, 630

[56] References Cited

U.S. PATENT DOCUMENTS

| 3,676,584 | 7/1972 | Plakas et al. | 73/628 |
| 3,847,016 | 11/1974 | Ziedonis | 128/660 |
| 3,948,248 | 4/1976 | Zuckerman et al. | 128/660 |
| 4,075,883 | 2/1978 | Glover | 128/660 |
| 4,154,114 | 5/1979 | Katz et al. | 128/660 X |
| 4,155,259 | 5/1979 | Engeler | 128/660 X |
| 4,233,987 | 11/1980 | Feingold | 128/639 |
| 4,241,611 | 12/1980 | Specht et al. | 128/660 X |
| 4,402,223 | 9/1983 | Naumann et al. | 73/628 X |

OTHER PUBLICATIONS

Thurstone et al., "Actual Time ... System", Ultrasonics Symposium Proceedings, IEEE Cat. #77CA 1264–1SU, 10/77.

Primary Examiner—Edward M. Coven
Attorney, Agent, or Firm—McAulay, Fields, Fisher, Goldstein & Nissen

[57] ABSTRACT

Apparatus for measuring corneal thickness. A transducer is provided that transducer includes a plurality of peizo-electric arcuate segments arranged in a circle to form an annular member. The segments are electrically and acoustically isolated from each other. Leads are connected to each segment for the transmission of electrical signals. The transducer is one component of a system for measuring corneal thickness. Also included in the system are a transmitter which is connected to the leads for applying an electrical signal to the segments to produce respective sound pulses, respective receivers connected to the leads for converting the signals into distance measurements, an averager capable of averaging the distance measurements and a display device to display the average distance.

6 Claims, 4 Drawing Figures ved transducer for use in
corneal measurements.

APPARATUS FOR MEASUREMENT OF CORNEAL THICKNESS

BACKGROUND OF THE INVENTION

The present invention relates to a transducer and apparatus for measuring corneal thickness.

Accurate measurement of corneal thickness has become more important with the introduction of a new operation for myopia called "radial keratotomy". In this operation a number of radial cuts are made in the cornea. The healed cuts result in scarring which in turn increases corneal refraction tending to reduce myopia. Since the cornea is very thin (approximately 0.6 mm) great care must be taken during this operation to insure that the cornea is not pierced. However, since the ultimate success of the operation improves with the deepness of the cut made, there is a desire to make the cut as deep as possible. To do this requires accurate knowledge of the thickness of the cornea for each patient It is also desirable to be able to map the cornea, since its thickness varies over its surface to some extent.

The use of ultrasonics in eye measurements is known and shown, for example, in U.S. Pat. No. 4,154,114, issued to L. Katz et al on May 15, 1979 and entitled "Biometric Measuring Device". Also, the use of small transducer at the end of a hand-held probe for determining the thickness of the cornea by conventional A-scan ultrasound methods is known in the art. The transducer is placed against the cornea. Echoes are received from the anterior and posterior surfaces of the cornea, and an electronic circuit measures the distance between the two faces by conventional techniques. To insure that the face of the transducer is perpendicular to the radius of curvature of the cornea, the electronic circuit prevents measurement unless the echos from the two faces meet some predetermined criteria concerning relative size. Thus, if the transducer is angulated by too great an amount, there will be no or only a small echo from the posterior surface and the system will indicate that the reading is not accurate. In spite of the foregoing, use of these systems do not give repeatable results. Thus, the expected and required accuracy is not achieved.

The principal reason for the aforementioned problem is that with the hand-held probe and the type of transducer used with said probe, the pressure applied to the cornea will almost always be so great as to deform the cornea enough to make the measurement useless. This excess pressure is due, in large part, to the flat configuration of the transducer which causes the user to apply excessive pressure in an attempt to obtain better contact with the curved surface of the cornea. It is also virtually impossible for users of current hand-held probes and simple transducers to maintain the holder and transducer perpendicular to the cornea. The cornea is very soft, and there will almost always be some angulation with present systems. Experience has shown that the aforementioned technique or comparing echoes from the two surfaces of the cornea is not sufficiently accurate. That is, with angulation portions of the cornea will be compressed and therefore indicate lesser than actual distances or depth of cornea. Further, the excess pressure results from the application, by the operator, of too much pressure on the probe in an effort to maintain the transducer in proper position on the eye.

Accordingly, it is an object of this invention to provide a transducer and apparatus for measuring corneal thickness which are capable of obtaining repeatable and accurate measurements.

It is a further purpose of this invention to provide such a transducer and apparatus which prevent the application of excess pressure to the cornea.

Another object of this invention is the provision of a transducer which can be easily maintained at the proper position on an eye without requiring the operator to apply excessive pressure on the transducer probe.

An additional object of the present invention is to provide an apparatus which insures that the measurement is taken with the transducer oriented perpendicular to the surface of the cornea.

BRIEF DESCRIPTION

In one embodiment of the invention, the apparatus includes a specifically developed transducer for use in corneal measurements.

The transducer includes a plurality of piezoelectric arcuate segments arranged in a circle to form an annular member. Insulating material, for electrically isolating each of the said plurality of segments from one another, is further provided. The transducer is constructed such that the plurality of segments are acoustically isolated from one another. Leads are connected to each of the segments for the transmission of electrical signals.

In addition to the transducer, the apparatus includes a transmitter connected to the leads for applying an electric signal to the segments to produce respective sound pulses; respective receiver means connected to each of the leads for converting the signal received from each associated segment into a distance measurement; an averager connected to each of the receivers to average the distance measured and thus indicate the distance measured at the center of the transducer; and display devices for displaying the average distance and the respective distances measured by each transducer segment.

The transducer and apparatus of the present invention will permit the accurate and repeatable measurement of corneal thickness and thus avoid the problems of prior art devices.

DESCRIPTION OF THE PREFERRED EMBODIMENTS

Figure 2:
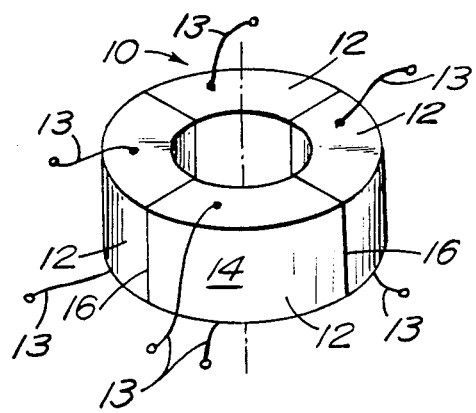
FIG. 2 is a perspective view of the transducer of the present invention.

Referring now to the drawing and more particularly to FIG. 2, reference numeral 10 denotes a transducer for use in the apparatus of the present invention for corneal measurement. The transducer 10 includes a plurality of piezo-electric arcuate segments 12 arranged in a circle to form an annular member 14. In a preferred embodiment of the present invention annular member 14 is constituted of between two through four arcuate segments, four 90° arcuate segments providing the most accurate, workable, transducer. Insulation means 16 is provided and constituted of any appropriate electrical insulator.

Each of the segments 12 is acoustically insulated from the other. This is accomplished by orienting the crystals so they vibrate only in the longitudinal direction (i.e., in a direction into the eye). Also the segments may be acoustically insulated from each other by connecting the segments 12 together by a mixture of rubber particles embedded in epoxy. Electrodes are plated on the front and rear faces of the transducer segments by standard techniques and leads may be connected thereto by any known method such as soldering. Other conventions practices which minimize cross-coupling may be used, and these practices will be known to those skilled in the art.

A sound-absorbing backing, using standard techniques well known in the field absorbs the backward-travelling wave so that it will not produce artifacts.

Respective lead means 13 are connected to the electrodes of each of the segments 12 for transmission of electrical signals, the crystals operating in the pulse-echo mode. Preferably, the lead means are constituted of a very light wire to prevent the addition of extra weight and pressure. Additionally the lead means are provided with adequate slack to also reduce said pressure, the slack preferably obtained by the provision of a large loop in the wire.

In a preferred embodiment of the present invention transducer 10 has an outer diameter of about 3.0 mm, an inner diameter of about 1.0 mm and a surface area of about 6.5 cm$^2$. Preferably, transducer 10 uses a resonant frequency of about 20 to 25 Mhz.

By forming transducer 10 as a segmented annular member 14, good contact with the curved surface of the cornea can be maintained without the application of too much pressure. The curved conformation of transducer 10 will naturally conform to the curvature of the cornea. Additionally, as will be explained more fully hereinafter, the provision of separate segments 12 affords means for indicating whether all of said segments are in good contact with the cornea. The transducer is constructed such that if all the segments are in contact with the cornea, the axis of the transducer will be along the radius of curvature of the cornea. This is an inherent feature of an annulus. While the transducer of the present invention requires high accuracy it does not require high resolution (the ability to distinguish between two closely spaced structures) and so, in use, the transducer of the present invention does not require high resolution and so moderate damping is suitable. As noted, each segment 12 of the transducer 10 is capable of operating independently in a pulse-echo mode.

In addition to the segmented annular transducer 10 and the respective leads discussed heretofore, the apparatus of the present invention includes a transmitter connected to the leads for applying electric signals to the plurality of segments 12 in order to produce respective sound pulses. Additionally the system includes receivers connected to each of the lead means for converting the signal received from each associated segment 12 into a signal representative of a distance measurement.

Respective averaging means are connected to each of the receivers to average the distance measurements and thus indicate the distance measured at the center of the transducer 10. The system additionally includes display means for displaying the average distance measured.

The time measurement circuitry used in the aforedescribed system is known and is described in detail in aforementioned U.S. Pat. No. 4,154,114. This known circuitry, in accordance with the system of the present invention, is multiplied by the number of segments 12. Hence in a preferred embodiment using four segments 12, the circuitry is multiplied four-fold.

Figure 1:
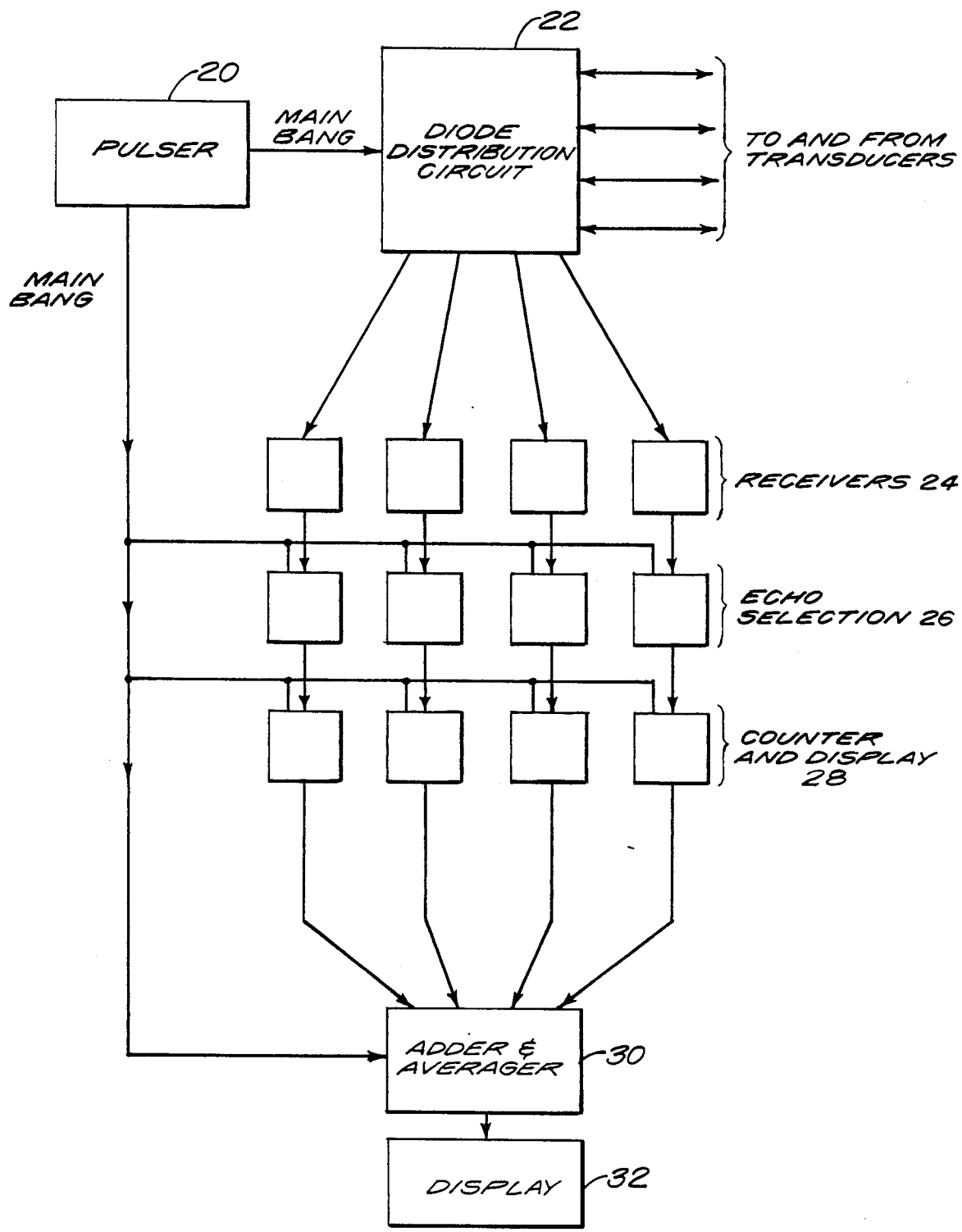
FIG. 1 is a schematic circuit diagram, in block form, of the apparatus of the present invention for the measurement of the thickness of the cornea.

As shown in FIG. 1, in a preferred embodiment a pulser 20 energizes the four segments 12 through a diode distribution circuit 22 which prevents cross-talk among the segments. The signals representing the respective echoes from each segment are returned through the distribution circuit and applied to a respective chain each of which includes a receiver 24 which detects and amplifies desired signals and apply the signals to echo selection circuits 26. The selection circuits 26 are effectively gates that pass the signals representing the echoes of interest. The signals are applied to counters 28 that convert the signals into distance measurements and apply the same to common adder and averager 30, which takes the sum and divides by 4. Each counter may include its own display. The average is also multiplied by the velocity of sound and then displayed by a display 32. Separate displays are used so the operator can verify that no angulation is present. That is, the thickness of the cornea does not change very rapidly from point-to-point. Thus, the thickness readings of the individual displays (i.e., the readings from the respective elements comprising the annulus) should be very close to the average. If the readings vary measurably, it could indicate that the annulus is, in fact, angulated.

The foregoing apparatus will give a measurement which is very close to the true measurement at the center of the annular member 14.

Using the foregoing apparatus, the present invention permits a person to easily and accurately measure corneal thickness.

Figure 3:
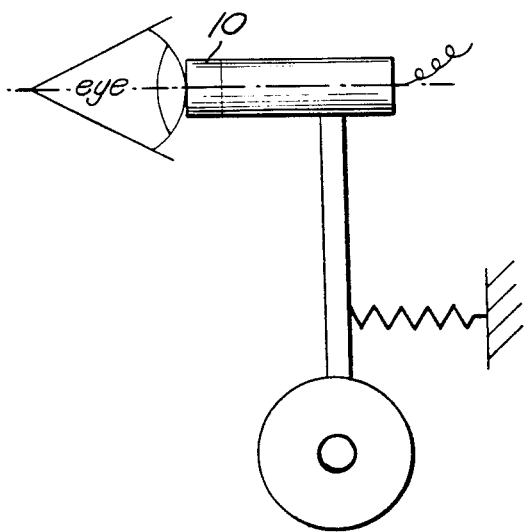
FIG. 3 is a schematic view showing the transducer of the present invention mounted on one type of tonometer.

In use, the transducer 10 is mounted in a support or carrier. The support carrier will allow a maximum force of 2.6 grams to be applied which results in negligible corneal compression. As best shown in FIG. 3 one appropriate carrier is a so-called Goldmann tonometer which is best suited for use with a slit-lamp and a seated patient. The support or carrier keeps the transducer in a fixed position. Once the transducer is perpendicular to the eye, as determined by methods shown later, the transducer will not change its orientation and will not compress because of the nature of the support.

Figure 4:
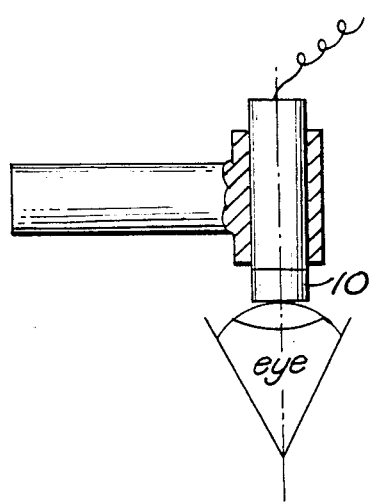
FIG. 4 is a further schematic view, partially in section, showing the transducer of the present invention mounted on another type of tonometer.

As best shown in FIG. 4 another appropriate support is a so-called Brunn-Jensen tonometer, which is best suited for use with a supine patient and which is not used with a slit lamp. The required force for both tonometers is about 1.23 grams, well within an acceptable limit for the apparatus of the present invention. Also, the transducer 10 is shown to greatly exaggerated scale in FIGS. 3 and 4 for purposes of explanation.

When using the apparatus of the present invention, the eye of the patient is anesthetized using conventional methods. The user then locates the portion of the eye to be measured. Depending upon which support is used, the patient is either seated or is supine.

Transducer 10 must be properly mounted in the carrier, or support and, as mentioned heretofore, care must be taken to insure that the leads going to the transducer do not add too much pressure.

For use with the Goldmann tonometer, transducer 10 may be encapsulated in a prism-holder using standard techniques. For use with the Brunn-Jensen tonometer, transducer 10 may be encapsulated in a weight by using standard techniques. Transducer 10 is then placed in an appropriate orientation such that it is perpendicular to the eye being measured. When the Goldmann tonometer is used, this appropriate orientation is horizontal. When the Brunn-Jensen tonometer is used, this appropriate orientation is vertical.

Transducer 10 is moved against the eye. Next the user observes the measurement displays from each of the segments 12. The measurement readings should all be approximately the same value if each of the segments 12 is making good contact with the eye. The holder mechanism insures that excess pressure is not applied against the eye. When all readings are approximately the same thus ensuring no angulation, the distance measurement from each segment is read. These separate readings are then averaged using the averager to thus obtain the distance measured at the center of the annular member 14. The average distance is then displayed on the display 32. That is, it can be shown mathematically that if the thickness of the cornea changes linearly, the average will be the correct thickness measured along the central axis of the transducer.

In use, the apparatus of the present invention provides a relatively easily operated and highly accurate way to measure corneal thickness thereby enabling, among other things, the safe and maximally effective performance of radial keratotomies.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed is:

1. Apparatus for the measurement of the thickness of the cornea comprising:

a piezo-electric transducer having a plurality of independent arcuate segments arranged in a circle to form a ring;

insulation means for electrically isolating each of said plurality of segments from the other;

acoustic means for acoustically isolating each of said plurality of segments from the other;

respective lead means connected to each of said plurality of segments for transmission of electrical signals;

a transmitter connected to said lead means for applying an electric signal to said plurality of segments to produce respective sound pulses;

respective receiver means connected to each of said lead means for converting the signal received from the associated segment into a distance measurement;

averaging means connected to all of said receiver means to average the distance measurements to thus indicate the distance measured at the center of said transducer; and display means for displaying the average distance.

2. The apparatus of claim 1, in which said receiver means includes respective display means to display the distance measured by each segment.

3. The apparatus of claim 1, wherein said plurality of segments of said transducer includes between two to four segments.

4. The apparatus of claim 3, wherein said plurality of segments of said transducer include four ninety degree segments.

5. The apparatus of claim 1, in which said receiver means comprises a plurality of circuits equal in number to said plurality of segments, each of said circuits comprising a receiver for receiving an electric signal from the associated segment, gate means for passing selected ones of said signals, and counter means for converting the passed signals into distance measurements.

6. The apparatus of claim 1, wherein said piezo-electric transducer has an outer diameter of substantially 3.0 mm, and an inner diameter of substantially 1.00 mm and a surface area of substantially 6.5 cm$^2$.

* * * * *